United States Patent [19]

Ikebe et al.

[11] Patent Number: 5,278,407
[45] Date of Patent: Jan. 11, 1994

[54] SECONDARY-ION MASS SPECTROMETRY APPARATUS USING FIELD LIMITING METHOD

[75] Inventors: Yoshinori Ikebe, Katsuta; Hifumi Tamura, Hachioji; Hiroyuki Sumiya, Ibaraki; Akemi Furuki, Sendai, all of Japan

[73] Assignees: Hitachi, Ltd., Tokyo; Hitachi Instrument Engineering Co., Ltd., Ibaraki, both of Japan

[21] Appl. No.: 873,173

[22] Filed: Apr. 24, 1992

[30] Foreign Application Priority Data

Apr. 25, 1991 [JP] Japan .................. 3-095520

[51] Int. Cl.⁵ .............................................. H01J 37/26
[52] U.S. Cl. ...................................... 250/309; 250/296
[58] Field of Search ...................... 250/251, 309, 296

[56] References Cited

U.S. PATENT DOCUMENTS

| | | | |
|---|---|---|---|
| 3,986,025 | 10/1976 | Fujiwara et al. | 250/309 |
| 4,510,387 | 4/1985 | Izumi et al. | 250/309 |
| 4,639,301 | 1/1987 | Doherty et al. | 250/251 |
| 4,939,360 | 7/1990 | Sakai | 250/398 |
| 5,086,277 | 2/1992 | Toita et al. | 250/309 |
| 5,164,596 | 11/1992 | Noguchi et al. | 250/309 |

*Primary Examiner*—Bruce C. Anderson
*Attorney, Agent, or Firm*—Antonelli, Terry, Stout & Kraus

[57] ABSTRACT

A secondary-ion mass spectrometry apparatus using a field limiting method includes an optical system for primary ions, a sample chamber, and an optical system for secondary ions, and a total ion monitor (TIM) interposed between an electric sector and a magnetic sector of the optical system for secondary ions. A field-limited image (or TIM image) from the TIM can be observed or monitored continually by a CRT, thereby making it possible to grasp quantitatively the charging state of a sample surface. The apparatus may further include an adjuster for adjusting quantatively the charging state of the sample surface.

10 Claims, 8 Drawing Sheets

| SCAN No. | TIME | $^{27}Al^+$ | $^{27}Al^{16}O^+$ | $^{27}Al_2^+$ |
|---|---|---|---|---|
| 1 | 1.2 | 1717433 | 159965 | 105527 |
| 2 | 2.4 | 1648136 | 161668 | 106446 |
| 3 | 3.6 | 1633626 | 159991 | 106651 |
| 4 | 4.8 | 1613437 | 159997 | 104425 |
| 5 | 6.0 | 1599921 | 157789 | 103882 |
| 6 | 7.2 | 1567600 | 157452 | 106680 |
| 7 | 8.4 | 1620355 | 164574 | 104622 |
| 8 | 9.6 | 1644268 | 159746 | 105374 |
| 9 | 10.8 | 1609422 | 158846 | 106741 |
| 10 | 12.0 | 1598260 | 156675 | 107215 |
| 11 | 13.2 | 1584995 | 159984 | 104956 |
| 12 | 14.4 | 1637041 | 159941 | 107684 |
| 13 | 15.6 | 1577951 | 152263 | 107100 |
| 14 | 16.8 | 1578196 | 162216 | 106609 |
| 15 | 18.0 | 1661414 | 162218 | 106746 |
| 16 | 19.2 | 1622540 | 161335 | 105876 |
| MEAN | | 1600000 | 160000 | 106000 |
| STANDARD DEVIATION | | 2 % | 2 % | 1 % |
| RELATIVE STANDARD DEVIATION | | 1 % | 1 % | 1 % |

SECONDARY-ION MASS SPECTROMETRY APPARATUS USING FIELD LIMITING METHOD

BACKGROUND OF THE INVENTION

The present invention relates to a secondary-ion mass spectrometry (SIMS) apparatus, and more particularly to a secondary-ion mass spectrometry apparatus using a field limiting method in which only ions generated from a sample portion to be analyzed are introduced into a mass spectrometer portion of the apparatus, thereby making it possible to acquire analysis data having high reliability.

A secondary-ion mass spectrometry apparatus is one in which secondary ions emitted from a sample surface by irradiation thereof with a primary ion beam are introduced into a mass spectrometer portion of the apparatus to make mass-spectrometric analysis of the secondary ions. When the sample surface is scanned with the primary ion beam, constituent elements of the sample surface are etched with the lapse of time, thereby allowing an elemental or component analysis of the sample in a depth direction thereof. This is disclosed by U.S. Pat. No. 3,894,233.

In the case where a sample is a conductor, charges produced on a surface of the sample are dissipated through the conductor sample even if the reception and release of charges including the irradiation of the sample surface with a primary ion beam and the emission of secondary ions and secondary electrons from the sample surface are made at the sample surface. However, in the case where the sample is an insulator, charges produced on the sample surface residue (or are accumulated) thereat and hence the sample surface is charged. Therefore, the energy of secondary ions emitted from the sample surface changes depending upon the charges accumulated on the sample surface. When such secondary ions are introduced into a mass spectrometer portion, the accuracy of mass-spectrometric analysis of secondary ions is affected.

A method of avoiding the charging phenomenon at the sample surface affecting the mass-spectrometric analysis of secondary ions including an electron spray method disclosed by JP-B2-54-6912. When a sample surface is irradiated with a primary ion beam so that secondary ions and secondary electrons are emitted from the sample surface, the sample surface is generally charged with positive charges. According to the electron spray method, the sample surface is irradiated with electrons in order to neutralize the positive charges with which the samples surface will otherwise be charged.

Another method of avoiding the charging phenomenon at the surface of an insulator sample is an electron bombardment induced conductivity (EBIC) method disclosed by Y. Ikebe et al. Seventh Int. Conference on SIMS, (1989) pp. 891-894. In the EBIC method, the sample surface is irradiated with electrons on the basis of the same principle as the electron spray method to form an electrically conductive layer on the sample surface in order that charges accumulated on the sample surface are dissipated through the conductive layer.

The two methods mentioned above are effective to the secondary-ion mass spectrometry apparatus but involve the following problems.

In the electron spray method, though it is intended to avoid the charging of the surface of an insulator sample by irradiating the sample surface with electrons, it is not possible to sufficiently neutralize charges accumulated on the sample surface. Further, no means for confirming the degree of neutralization is provided.

In the EBIC method, the conductive layer formed by the EBIC method may be extinguished as the analysis of the sample surface for layers to be analyzed along a depth direction progresses with the lapse of time. As a result, a charging phenomenon may be generated again at the sample surface or the charging state of the sample surface may change. No means for quantitatively discriminating such a change of the charging state is provided.

Namely, in the above-mentioned insulator analysis methods used in the conventional SIMS apparatus, no consideration is taken for (1) the provision for confirming the avoidance of charging and (2) the provision for quantitatively discriminating the change in charging state. Accordingly, in the analysis of insulator by the prior art, it is not possible to quantitatively grasp the charging state and hence the reliability of data acquired is greatly questionable.

As a further prior art is known a secondary-ion mass spectrometry apparatus using a field limiting method disclosed by H. Tamura et al. "DEVELOPMENT OF A NEW FIELD LIMITING METHOD FOR SIMS", SIMS VII, (1989) pp. 903-906. In the case where the mass-spectrometric analysis of constituent elements of a sample surface is conducted by scanning the sample surface with a primary ion beam while deflecting the beam, the analysis progresses to the constituent elements of a more deep layer of the sample gradually with the lapse of time. Generally, in that case, secondary ions emitted from the vicinity of the edge portion of a sample surface scanning region of the primary ion beam originate from a layer shallower than a layer from which secondary ions are emitted from the vicinity of a central portion of the scanning region. Therefore, the accuracy of component analysis of each layer for the depth direction of the sample becomes poor. According to the field limiting method, secondary ions emitted at the edge portion of the sample surface scanning region of a primary ion beam are intercepted and only secondary ions emitted at the central portion of the scanning region are introduced into a mass spectrometer portion of the apparatus.

SUMMARY OF THE INVENTION

An object of the present invention is to provide a secondary-ion mass spectrometry (SIMS) apparatus which contemplates adjusting quantitatively the charging state of a sample surface and grasping quantitatively the charging state of the sample surface.

In an SIMS apparatus of the present invention, a total ion monitor is interposed between an electric sector and a magnetic sector of an optical system for secondary ions and observing means is provided with which the deviation of the trajectory of secondary ions caused by the charge potential of a sample surface is directly observed as a field-limited image by using a field limiting method in combination with the total ion monitor.

The apparatus may be provided with adjusting means for adjusting quantitatively the deviation of the secondary ion trajectory by use of the field-limited image.

The apparatus may be provided with means for grasping quantitatively the charging state of a sample surface upon analysis of the sample by use of the field-limited image.

DESCRIPTION OF THE PREFERRED EMBODIMENTS

Embodiments of the present invention will now be explained in reference to the accompanying drawings.

Figure 1A:
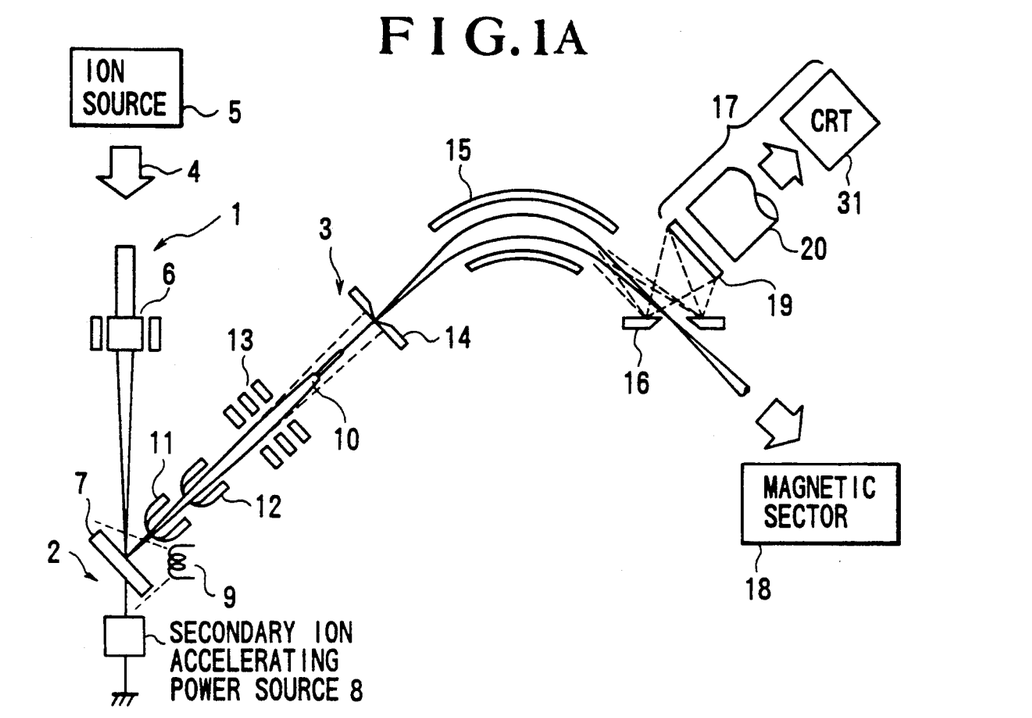
FIG. 1A is a diagram showing the construction of an SIMS apparatus according to an embodiment of the present invention.
Figure 1B:
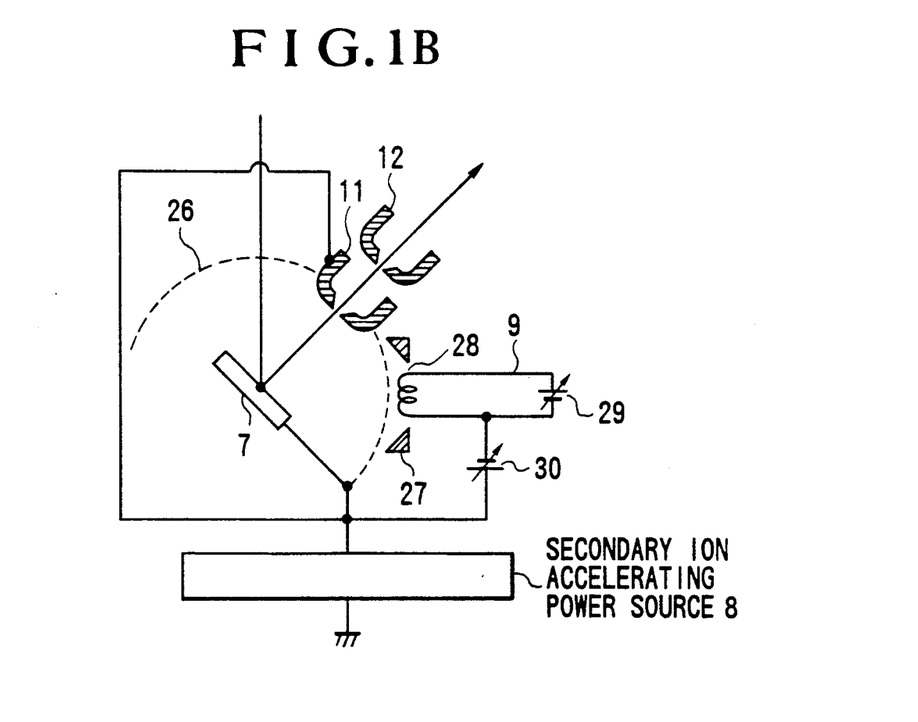
FIG. 1B is a diagram showing the details of a main part of the apparatus shown in FIG. 1A.
Figure 1C:
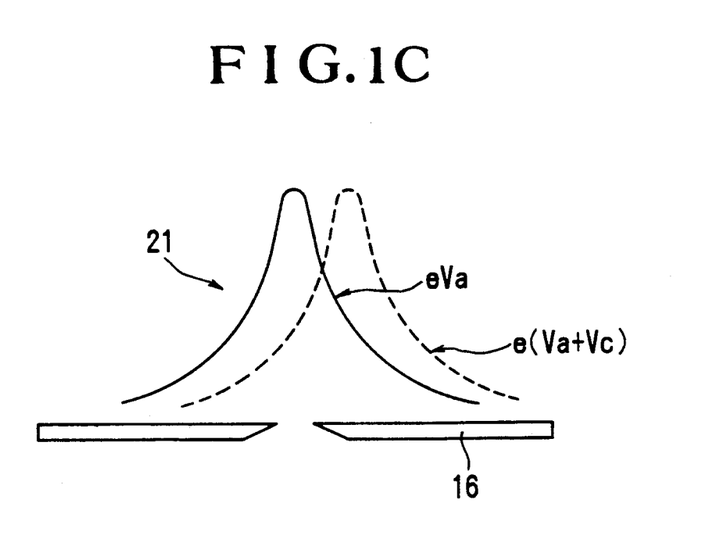
FIGS. 1C and 1D are diagrams for explaining the principle of the present invention.
Figure 1D:
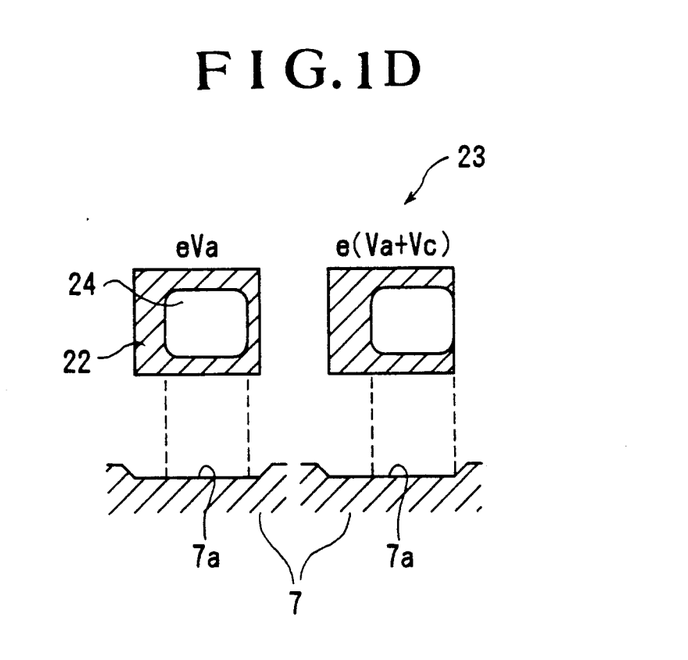

FIGS. 1A and 1B show an SIMS apparatus according to an embodiment of the present invention, and FIGS. 1C and 1D are diagrams for explaining a relationship between the deviation of a secondary ion trajectory caused by a charging phenomenon and a field-limited image.

Referring to FIG. 1A, the SIMS apparatus includes an optical system 1 for primary ions, a sample chamber 2 and an optical system 3 for secondary ions. The optical system 1 for primary ions is composed of an ion source 5 for generating a primary ion beam 4 and a deflector electrode 6 for making a raster scan of the primary ion beam 4. The sample chamber 2 is composed of a mounting portion for a sample 7, a secondary ion accelerating power source 8, and an electron spray portion 9 for irradiating the surface of the sample 7 with an electron beam when the sample 7 is an insulator. The optical system 3 for secondary ions is composed of an extractor electrode 11 for extracting secondary ions 10, a post-accelerator electrode 12, a projection lens 13 for focusing the secondary ions 10 onto an exit slit 14 (which may also be called a field limiting slit), the exit slit 14 for passing therethrough the focused secondary ions 10 in a limiting manner, an electric sector 15 for energy-separating the secondary ions, a total ion monitor 17 (hereinafter referred to TIM) for observing a field-limited slit image (or TIM image) on a $\beta$ slit 16, and a magnetic sector 18 for mass-separating the secondary ions.

The TIM 17 includes an scintillator 19 for capturing electrons emitted from the $\beta$ slit 16 by the bombardment thereof with the secondary ions 10, and a photomultiplier 20 for detecting a signal from the scintillator 19. A TIM signal obtained is displayed as a TIM image by a CRT 31.

As shown in more detail by FIG. 1B, the sample chamber includes a mesh portion 26 provided so as to enclose the sample 7. The mesh portion 26 is connected to the secondary ion accelerating power source 8 and the extractor electrode 11. The electron spray portion 9 has a filament electrode 28 at a central portion of a pierce electrode 27, and a heating current of the filament electrode 28 can be adjusted by a filament power source 29. A potential of the filament electrode 28 with respect to the sample 7 can be adjusted by a variable voltage source 30.

A primary ion beam scans the surface of the sample 7 by virtue of the action of the deflector electrode 6. In order that secondary ions emitted from the sample surface are focused at the position of the exit slit (or field limiting slit) 14, that part of the secondary ions emitted from the sample surface which are emitted from an approximately peripheral portion of a region of the sample surface scanned by the primary ion beam is intercepted by the exit slit 14 or is prevented from entering the electric sector 15. Accordingly, only that part of the secondary ions emitted from the sample surface which are emitted from an approximately central portion of the sample surface scanning region of the primary ion beam, is introduced into the electric sector 15. Thereby, a limited field or a field limitation is established.

The electric sector 15 has a function of energy-separating the secondary ions. Therefore, that part of ions passed through the electric sector 15 which have an energy higher or lower than a predetermined energy, is prevented by the $\beta$ slit 16 from being introduced into the magnetic sector 18, as shown by broken line.

The total ion monitor 17 outputs a detection signal for display on the CRT in synchronism with a deflecting action of the deflector electrode 6. On the CRT is displayed a sample surface image field-limited by the exit slit 14, as shown on the left side of FIG. 1D. Referring to the shown image, an outer frame 22 of the image represents the scanning region of the primary ion beam, a shaded portion represents a portion where secondary ions are intercepted by the exit slit 14, and a central bright (or clear) portion 24 is a region where secondary ions are taken in a mass spectrometer portion.

As has been mentioned above, an emission pattern of secondary ions generated from the sample surface by irradiation thereof with a primary ion beam is imaged at the position of the exit slit 14 by the projection lens 13. The field of the emission pattern is limited by the exit slit (or field limiting slit) 14 so that secondary ions generated from the peripheral portion of the scanning region of the primary ion beam are cut off and only desirable secondary ions generated from the central portion of the scanning region of the primary ion beam are introduced into the mass spectrometer portion. At this time, a bright field on the exit slit 14 is observed directly by the CRT 31. The above process is called a field limiting method combined with a total ion monitor (TIM). Thus, the field limiting method combined with the TIM is used for observing directly the deviation of the secondary ion trajectory due to the sample surface charge potential as a TIM image on one hand to adjust quantitatively the charge potential of the sample surface and for monitoring continually the TIM image upon analysis on the other hand in order that the charging state of the sample surface can be grasped quantitatively.

In the case where the charge potential of the sample surface is 0, the emission pattern is imaged at the center position of the exit slit 14 and hence a central portion of the secondary energy distribution is passed through a central portion of the $\beta$ slit 16. Therefore, an image of the exit slit 14 is correspondingly projected on the $\beta$ slit 16 as it is. Accordingly, the TIM image is observed with a form in which the central portion of the scanning region of the primary ion beam is positioned at a central portion of the image. On the other hand, in the case where a charge potential is produced on the sample surface, the emission pattern is imaged deviating from the center position of the exit slit and hence an edge portion of the emission pattern is passed through the $\beta$ slit. Therefore, the TIM image is observed with a form in which the central portion of the scanning region of the primary ion beam is positioned at an end or edge portion of the image. Thus, it is possible to observe the deviation of the secondary ion trajectory due to the sample surface charge potential directly and continually by means of the TIM image.

In the above SIMS apparatus, in the case where the sample 7 is a conductor, the charge potential of the sample surface is 0 even if the sample surface is irradiated with a primary ion beam. Therefore, provided that a power voltage of the secondary ion accelerating power source 8 is $V_a$, the initial energy of secondary ions 10 is $eV_a$ eV (electron volt) and the secondary ions 10 take a trajectory shown by solid line in FIG. 1A. On the other hand, in the case where the sample 7 is a semiconductor or an insulator, the surface of the sample 7 is charged to a charge potential $V_c$ V (volt) by irradiation with a primary ion beam and hence the initial energy of secondary ions 10 becomes $e(V_a+V_c)$ eV. Therefore, the secondary ions 10 take a deviated trajectory as shown by dotted line in FIG. 1A. Owing to this deviation of the secondary ion trajectory, a secondary ion energy distribution 21 on the $\beta$ slit 16 is shifted from a position shown by solid line to a position shown by dotted line (see FIG. 1C). Accordingly, a TIM image 23 on the scanning region 22 of the primary ion beam (displayed on the CRT) results in a shifted image, as shown on the right side of FIG. 1D.

Namely, in the case where the charge potential is 0, only a central portion of a secondary ion signal is passed through a central portion of the $\beta$ slit 16 and a secondary ion take-in region (or TIM image) 24 at that time is positioned at a central portion of the scanning region of the primary ion beam 4. This means that only secondary ions from a central portion of an etching crater 7a of the surface of the sample 7 formed by the primary ion beam 4 are taken in. On the other hand, in the case where the charge potential is $V_c$ V, a skirt portion of the secondary ion signal is passed through the $\beta$ slit 16 and hence the TIM image is positioned at an end portion of the scanning region 22 of the primary ion beam. This means that secondary ions from an edge portion of the etching crater 7a are taken in. From the foregoing, it can be understood that the deviation of the secondary ion trajectory due to the charging phenomenon can be observed directly as the TIM image 23.

An actual influence of the deviation of the secondary ion trajectory on an elemental analysis in a depth direction will now be explained in reference to FIGS. 2A and 2B. In the figures, the abscissa of each graph represents a time (or depth) and the ordinate represents the relative intensity of secondary ions. In each graph, a field-limited image and an etching crater are also shown.

Figure 2A:
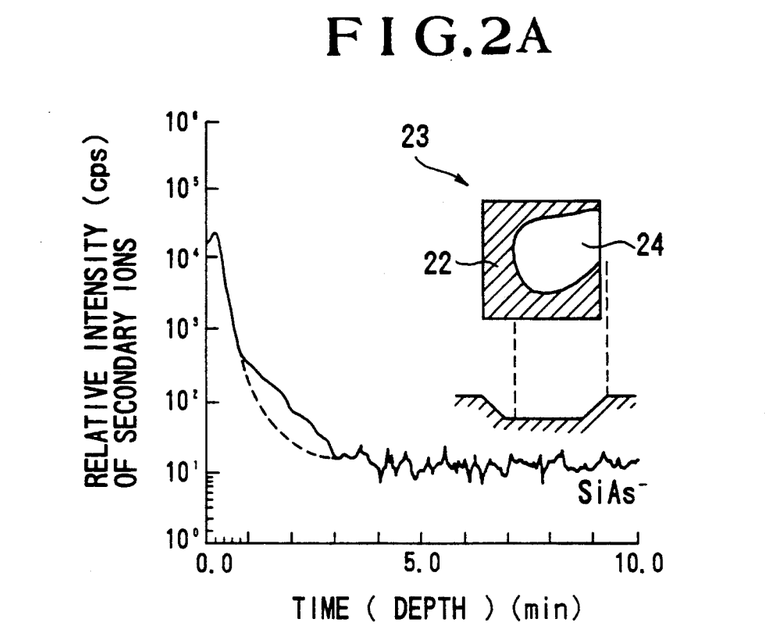
FIGS. 2A and 2B are graphs each showing a relationship between a field-limited image and an elemental profile in a depth direction.
Figure 2B:
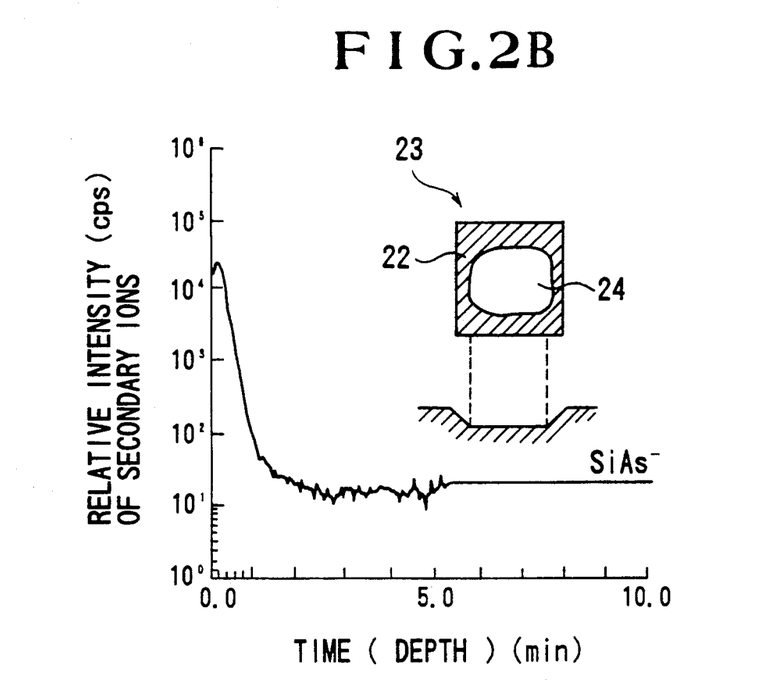

In the case where a TIM image is adjusted as for a metal surface to be positioned at the central portion of the scanning region and a $^{28}$Si ion doped GaAs wafer of high resistivity is thereafter analyzed, the TIM image is shifted to the right end of the scanning region due to a shift of the initial energy of secondary ions caused by a contact potential difference between the metal and GaAs, as shown in FIG. 2A, so that an AsSi profile has a shoulder on a skirt portion owing to a crater edge effect. On the other hand, in the case where a TIM image is adjusted as for a GaAs surface and measurement or analysis is thereafter made, an AsSi profile obtained exhibits a profile having no shoulder, as shown in FIG. 2B, since only secondary ions from the center portion of the crater are taken in. From the above, it can be understood that a minute contact potential difference has a great influence on the deviation of the secondary ion trajectory.

Figures 3A, 3B, 3C:
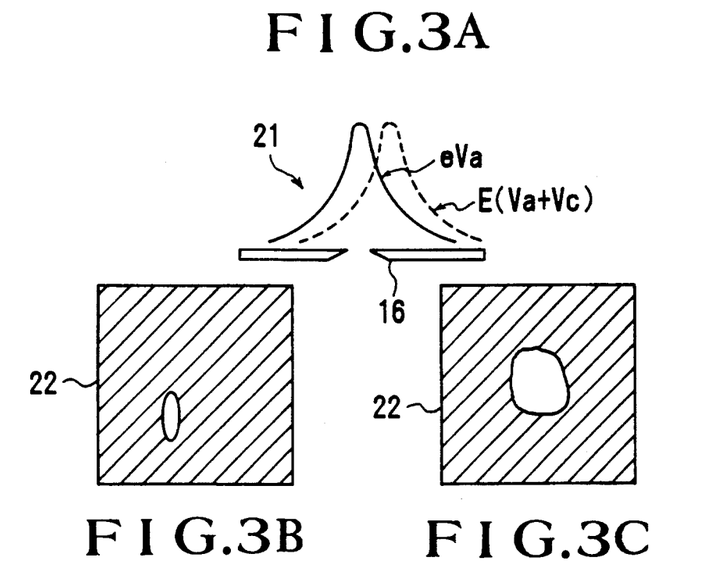
FIGS. 3A to 3C are diagrams for explaining the quantitative adjustment of the charge potential of a sample surface using a field-limited image and an electron spray method.

Next, explanation will be made of means of the present invention for adjusting quantitatively the charge potential of the sample surface by use of an electron spray method while observing the TIM image. The explanation will be made referring to FIGS. 3A to 3C. A bulk-like insulator AIN is used as a sample. In the case where the initial energy of secondary ions has been changed to $e(V_a+V_c)$ eV owing to the charge potential of $V_c$ V, a secondary ion energy distribution is shifted on the $\beta$ slit 16, as shown by broken line in FIG. 3A, and a TIM image exhibits a little appearance at the left and lower portion of the scanning region 22, as shown in FIG. 3B. If the sample surface in such a state is gradually irradiated with an electron beam by the electron spray portion 9 with the filament power source 29 and the variable voltage source 30 being adjusted, the TIM image is gradually shifted toward the central portion of the scanning region 22 so that a TIM image having a high brightness and a clear contour ultimately appears at the central portion of the scanning region 22, as shown in FIG. 3C. In this manner, the deviation of the secondary ion trajectory due to the charge potential can be adjusted quantitatively while observing the TIM image.

A method for analysis of a multi-layer insulator sample using a technique according to the present invention will now be explained in reference to FIGS. 4 to 7.

Figure 4A:
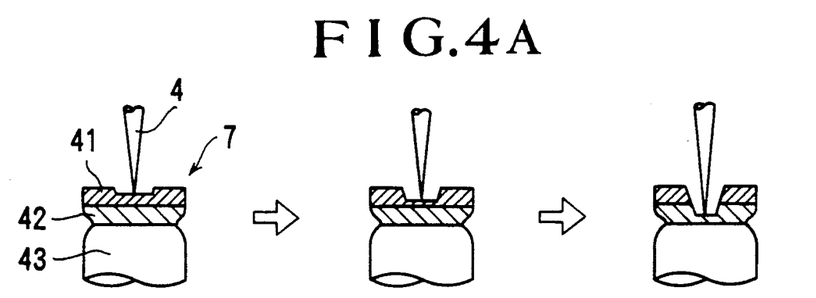
FIGS. 4A to 4D are diagrams showing the change of a field-limited image upon elemental analysis of an Al layer and an $SiO_2$ layer in a depth direction in a state in which the prevention of charging is not made.
Figure 4B:
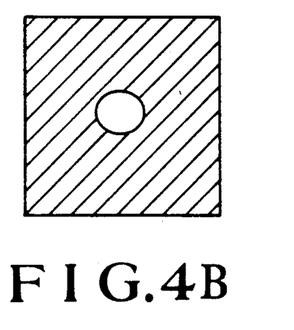
Figure 4C:
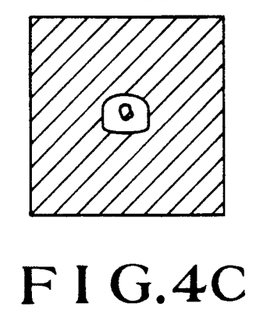
Figure 4D:
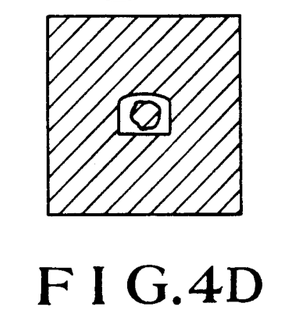

As shown in FIG. 4A, a sample 7 used in the present embodiment is a three-layer insulator sample which includes an Al layer 41, an SiO$_2$ layer 42 and an Si substrate 43. In FIG. 4A, three stages of process are shown in regard to the analysis of the sample. FIGS. 4B to 4D show TIM images corresponding to the three stages of process for a change in TIM image upon measurement of an Al profile for the Al layer and the SiO$_2$ layer in a state in which the prevention of charging is no made.

Figure 5:
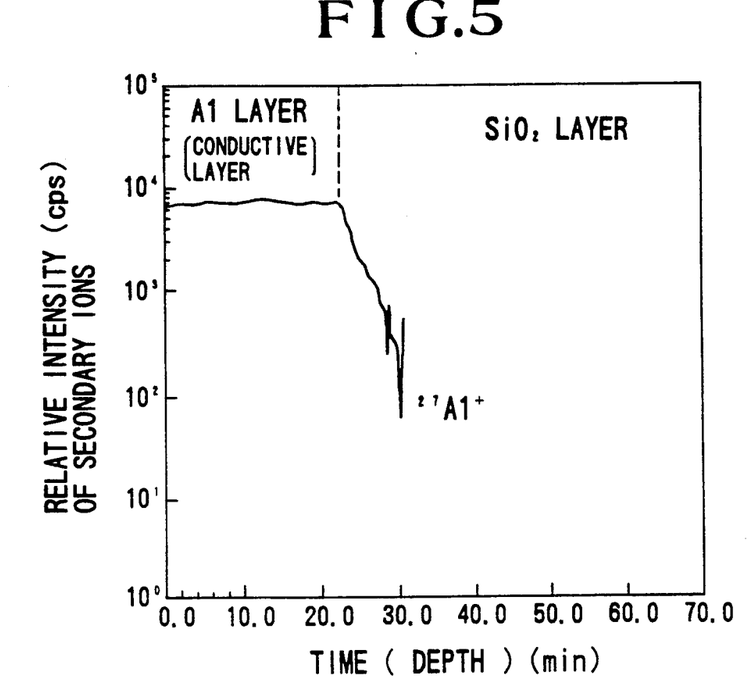
FIG. 5 shows an elemental profile of the Al layer and the $SiO_2$ layer in the state in which the prevention of charging is not made.

First, the measurement of an elemental or Al profile in a depth direction is started after a secondary ion trajectory has been adjusted by means of a TIM image as for the Al layer which is a conductor, as shown in FIG. 4B. When a primary ion beam 4 gets near to the SiO₂ insulator layer 42 with the progression of sputtering, a central portion of the TIM image becomes dark, as shown in FIG. 4C, due to the generation of a localized charging at a central portion of the sample surface. When the primary ion beam 4 reaches the SiO₂ insulator layer 42, the central portion of the TIM image becomes completely dark, as shown in FIG. 4D, with the result that secondary ions are not introduced into the magnetic sector 18 and hence the measurement of the Al profile becomes impossible, as shown in FIG. 5. The above shows that the measurement of the Al profile becomes impossible due to the generation of the localized charging even if the charge potential is adjusted prior to measurement and that such a charging state can be monitored continually.

Figure 6A:
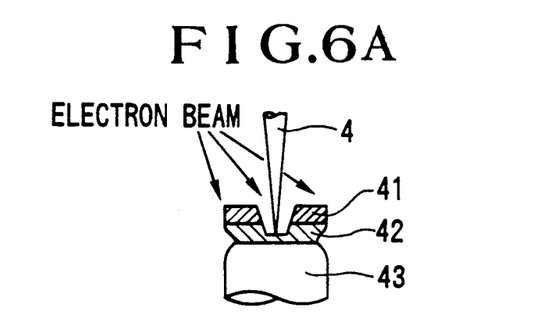
FIGS. 6A to 6D are diagrams for explaining a process in which the surface charge potential of a sample including an Al layer and an $SiO_2$ layer is neutralized while observing a field-limited image for the $SiO_2$ layer.
Figure 6B:
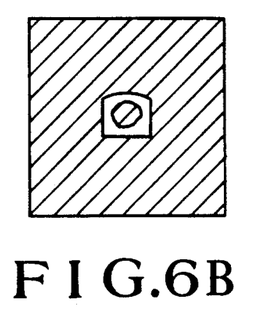
Figure 6C:
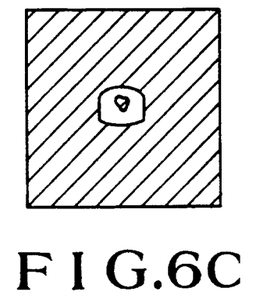
Figure 6D:
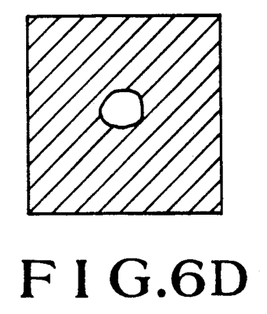
Figure 7:
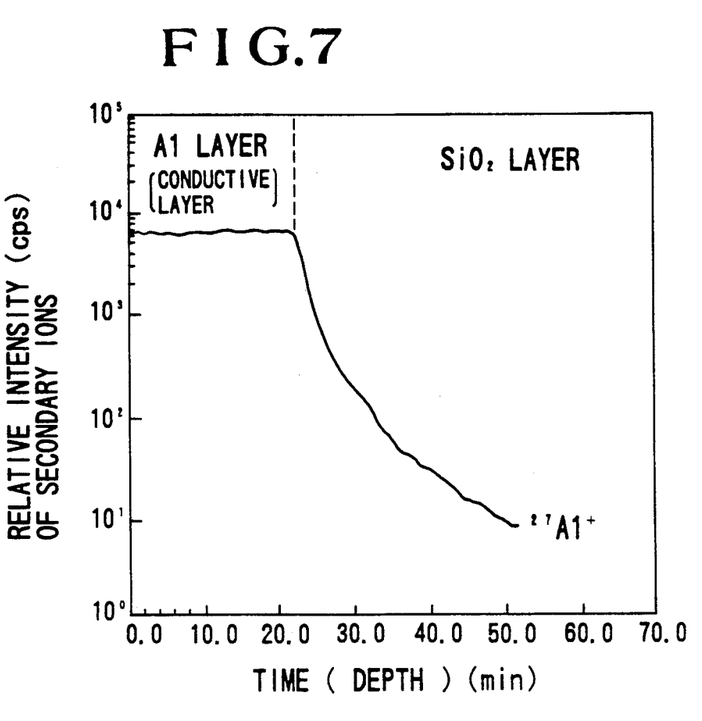
FIG. 7 shows an elemental profile of the Al layer and the $SiO_2$ layer in a depth direction after the charge potential has been adjusted.

Next, a method for adjustment of the charge potential of the sample as mentioned above will be explained by use of FIGS. 6A to 6D. When the SiO₂ insulator layer 42 comes to be irradiated with the primary ion beam 4, as shown in FIG. 6A, a TIM image as shown in FIG. 6B is first observed. If the sample 7 in such a state is gradually irradiated with an electron beam by the electron spray portion 9, a central portion of the TIM image becomes gradually bright, as shown in FIG. 6C. When the quantity of electron beam radiation or the amount of electron spray is gradually increased, the TIM image becomes completely bright, as shown in FIG. 6D. The above shows that the prevention of charging has completely been attained by the electron spray method. An Al profile measured under such a condition is stably displayed, as shown in FIG. 7, even after the primary ion beam has reached the SiO₂ insulator layer.

Figure 8:
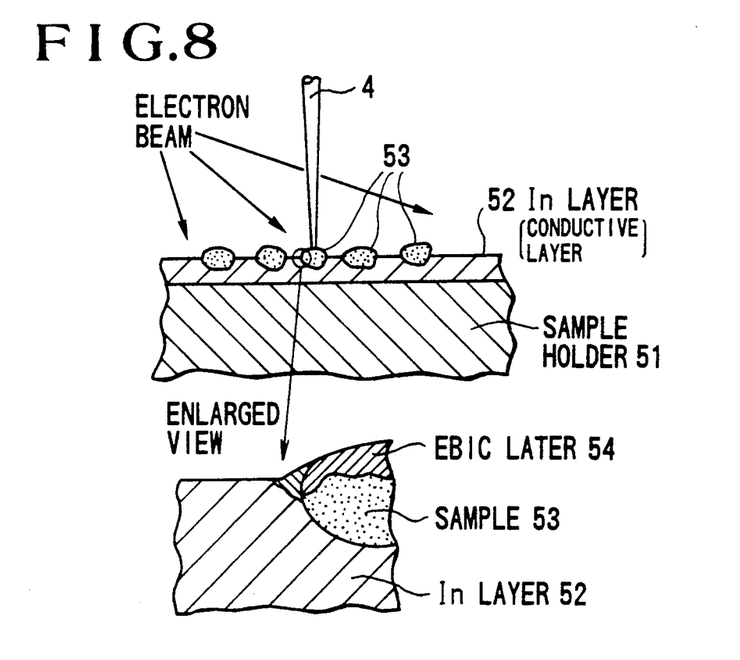
FIG. 8 is a partial cross section for explaining a sample holding method in the case where a sample is small in size.
Figure 9:
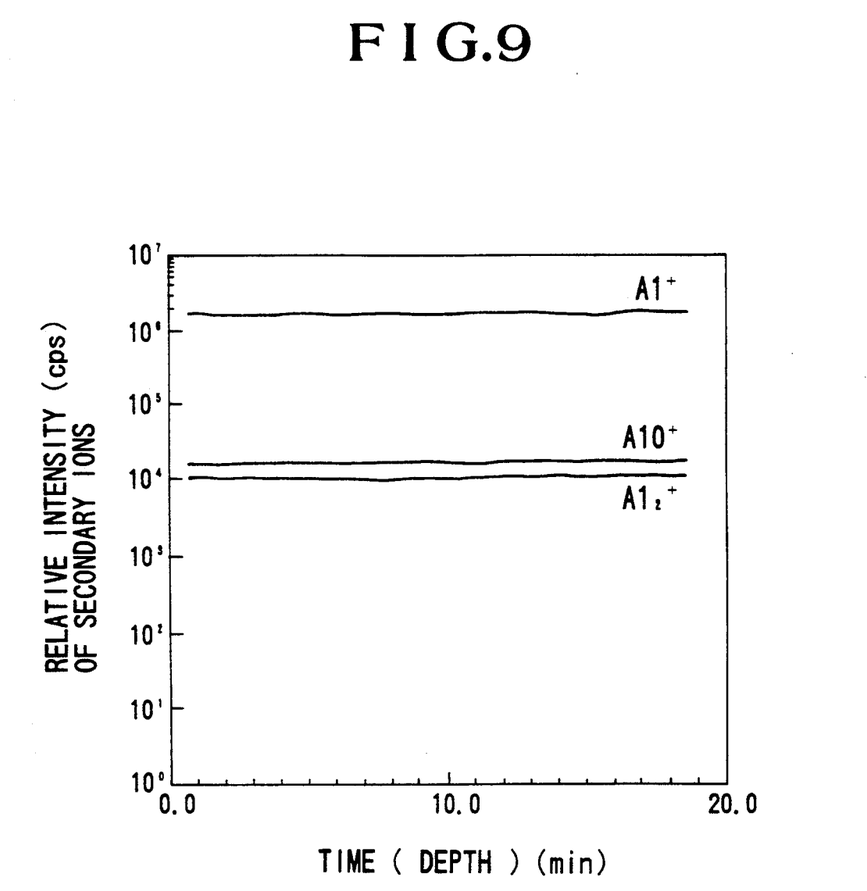
FIG. 9 shows an elemental profile of an insulator sample of $Al_2O_3$ powder or particles in a depth direction.
Figure 10:
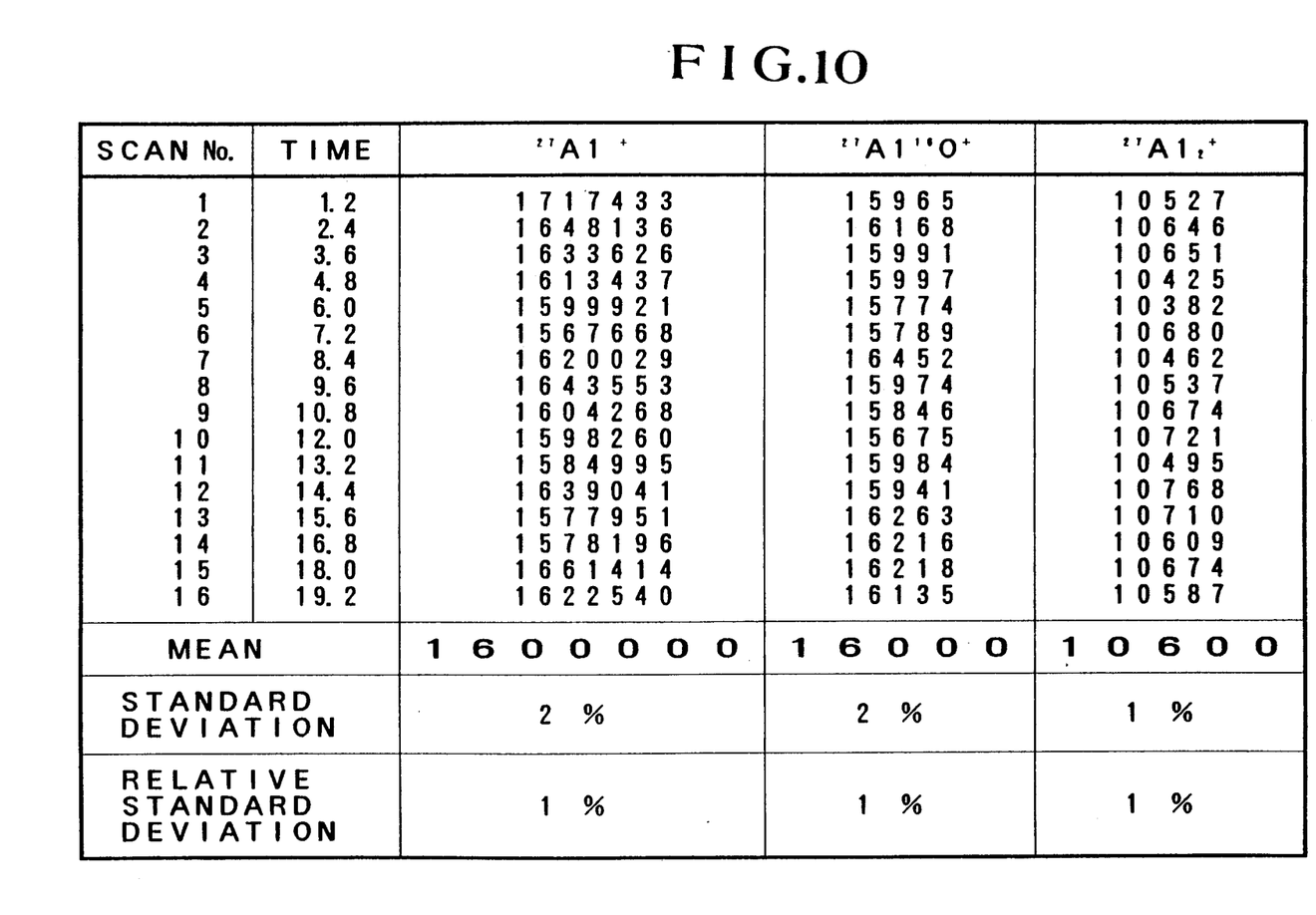
FIG. 10 is a table showing the result of estimation of the stability of the secondary ion intensity for the insulator sample of $Al_2O_3$ powder.

Finally, explanation will be made of an example of measurement of which the present invention is applied. A sample used is Al₂O₃ particles having a diameter not larger than several microns. FIG. 8 shows a sample holding method in the case where the sample is small in size. An In layer 52 is formed on a sample holder 51 and Al₂O₃ particles 53 are sprayed on the In layer 52. Thereafter, the In layer 52 is fused by means of a soldering gun or iron so that the Al₂O₃ particles 53 are fixed. The sample (or Al₂O₃ particles 53) subjected to such a pretreatment is irradiated or bombarded with an electron beam. Thereby, an electron bombardment induced conductivity (EBIC) layer 54 is formed through a thin film of the In layer 52 around the sample particles 53, as apparent from an enlarged view shown in FIG. 8. In this state, the prevention of charging is completely made in accordance with the technique taught by the present invention and measurement is thereafter made. FIG. 9 shows Al, AlO and Al₂ profiles measured. As shown, each profile is stable. The result of estimation of the stability of the secondary ion intensity is demonstrated by a table shown in FIG. 10. As seen from the table, a fluctuation in secondary ion energy was about 2% and a relative standard deviation indicative of a fluctuation in ion intensity was 1%, that is, a satisfactory result was obtained.

As apparent from the foregoing, according to the present invention, a field limiting method combined with a TIM is used in the analysis of an insulator, thereby making it possible to adjust the charge potential of the surface of a sample quantitatively and making it possible to grasp the charging state quantitatively. As a result, data with high reliability can be acquired.

We claim:

1. A secondary-ion mass spectrometry apparatus using a field limiting method, comprising:
   an optical system for primary ions for converging primary ion emitted from an ion source as a primary ion beam to irradiate a sample with the primary ion beam;
   a sample chamber for accommodating said sample irradiated with the primary ion beam from said optical system for primary ions, said sample chamber including electron spray means for effecting a spray of electrons onto said sample;
   an optical system for secondary ions including an optical imaging system for imaging secondary ions emitted from said sample by irradiation thereof with the primary ion beam, an exit slit for passing therethrough only secondary ions emitted from a predetermined secondary ion emitting area on said sample, an electric sector for energy-separating secondary ions passed through said exit slit and a $\beta$ slit for passing there-through those ones of the secondary ions energy-separated by said electric sector which have a predetermined energy;
   displaying means for displaying a sample image field-limited by said exit slit on the basis of secondary ions captured by said $\beta$ slit;
   a magnetic sector for analyzing secondary ions passed through said $\beta$ slit; and
   means for adjusting the electron spray means while displaying said sample image.

2. A secondary-ion mass spectrometry apparatus according to claim 1, wherein said optical system further includes deflecting means for scanning a surface of said sample with said primary ion beam.

3. A secondary-ion mass spectrometry apparatus according to claim 2, wherein said displaying means includes a CRT display device for displaying the field-limited sample image in synchronism with the scanning by said deflecting means.

4. A secondary-ion mass spectrometry apparatus according to claim 1, wherein said electron spray means includes a filament for emitting electrons and means for adjusting the amount of electron spray.

5. A secondary-ion mass spectrometry apparatus according to claim 4, wherein said electron spray amount adjusting means includes means for adjusting a current supplied to said filament.

6. A secondary-ion mass spectrometry apparatus according to claim 4, wherein said electron spray amount adjusting means includes means for adjusting the potential of said filament with respect to said sample.

7. A secondary-ion mass spectrometry apparatus according to claim 1, wherein said displaying means includes means for observing said field-limited sample image to observe a charging state of a surface of said sample.

8. A secondary-ion mass spectrometry apparatus according to claim 7, wherein said sample chamber includes means for neutralizing the charging state of the sample surface while observing the charging state by said displaying means.

9. An apparatus according to claim 1, wherein said means for adjusting the electron spray means adjusts an amount of the electron spray.

10. An apparatus according to claim 1, wherein said means for adjusting the electron spray means adjusts an energy of the electron spray.

* * * * *